United States Patent [19]

Wanderer et al.

[11] Patent Number: 5,030,209
[45] Date of Patent: Jul. 9, 1991

[54] HOLDER FOR DOUBLE ENDED BLOOD COLLECTION RETRACTABLE NEEDLE

[75] Inventors: Alan A. Wanderer, Englewood; William E. Sagstetter, Denver; William R. King; James W. Schreiber, both of Lakewood; Randal D. Bjerke, Boulder, all of Colo.

[73] Assignee: Medical Safety Products, Inc., Denver, Colo.

[21] Appl. No.: 269,168

[22] Filed: Nov. 9, 1988

[51] Int. Cl.⁵ .............................................. A61M 5/32
[52] U.S. Cl. .................................................... 604/198
[58] Field of Search ............... 128/763, 770; 604/187, 604/192, 197, 198, 263, 403, 415

[56] References Cited

U.S. PATENT DOCUMENTS

| | | | |
|---|---|---|---|
| 4,664,654 | 5/1987 | Strauss | 604/198 |
| 4,723,943 | 2/1988 | Spencer | 604/263 |
| 4,790,827 | 12/1988 | Haber et al. | 604/198 |
| 4,813,426 | 3/1989 | Haber et al. | 604/198 |

Primary Examiner—Max Hindenburg
Attorney, Agent, or Firm—Cahill, Sutton & Thomas

[57] ABSTRACT

A holder includes a double ended needle supporting insert translatable within a cylinder for receiving a blood collection tube during a medical procedure. Upon translation of the insert posteriorly, the double ended needle becomes fully enclosed within the cylinder and the insert is locked in place to shield the double ended needle from contact by medical personnel. An adapter fits within the insert to accommodate pediatric tubes.

46 Claims, 6 Drawing Sheets

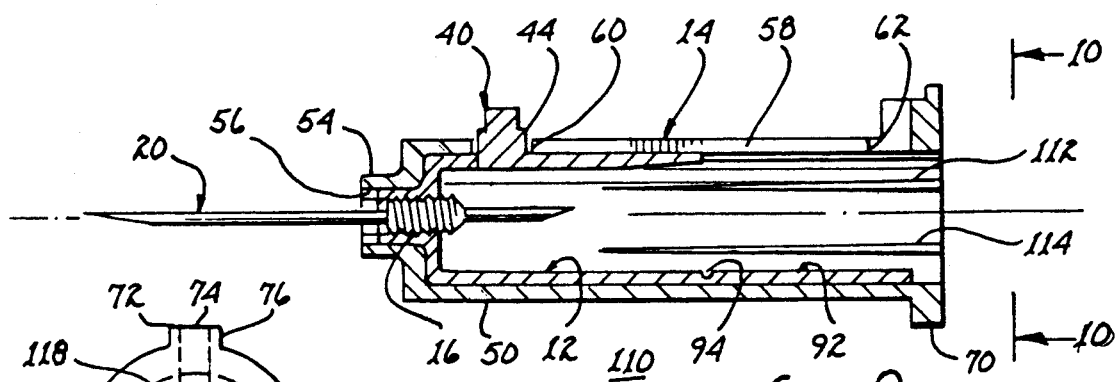
fig. 9
fig. 10
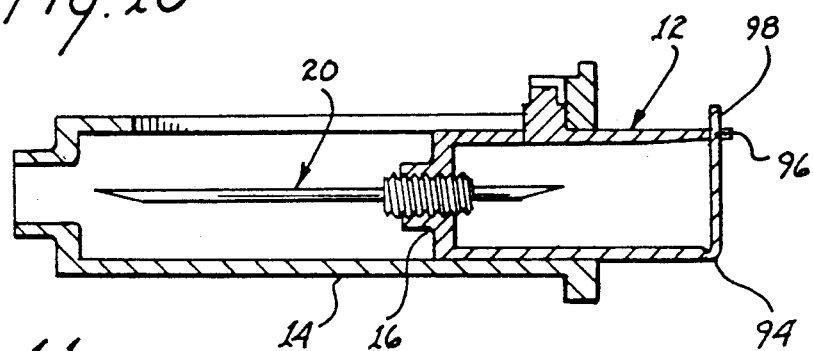
fig. 11
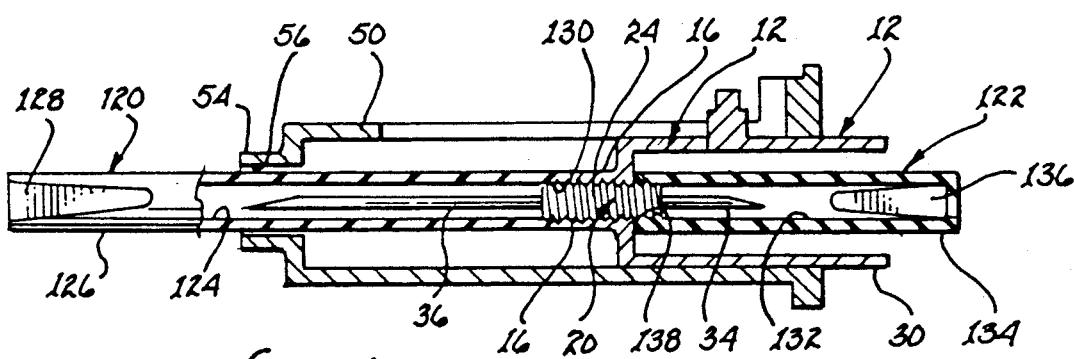
fig. 12
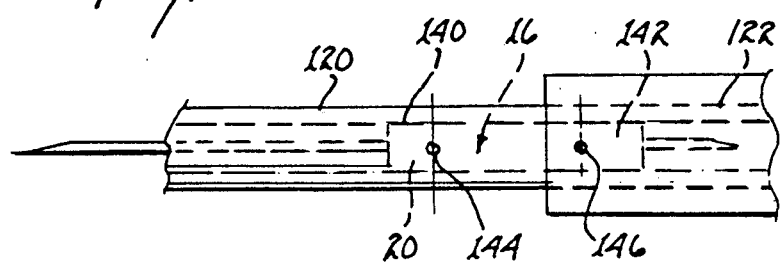
fig. 13

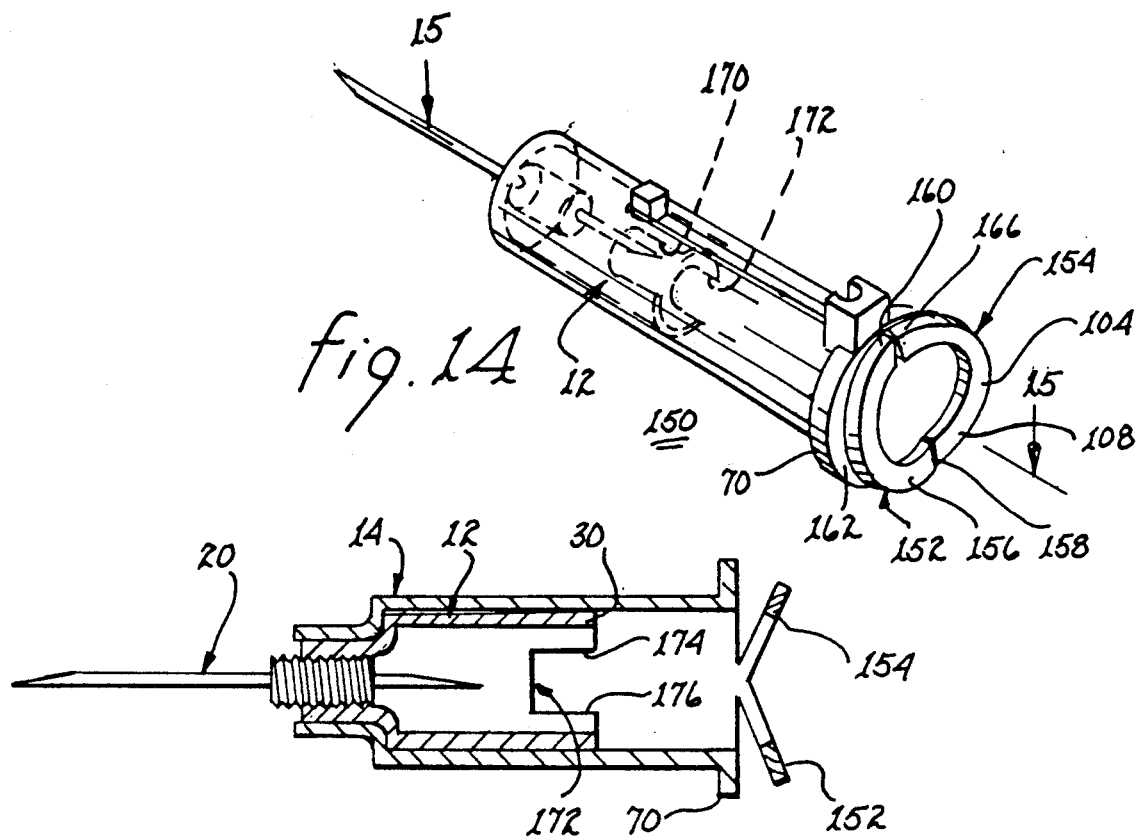
fig. 14
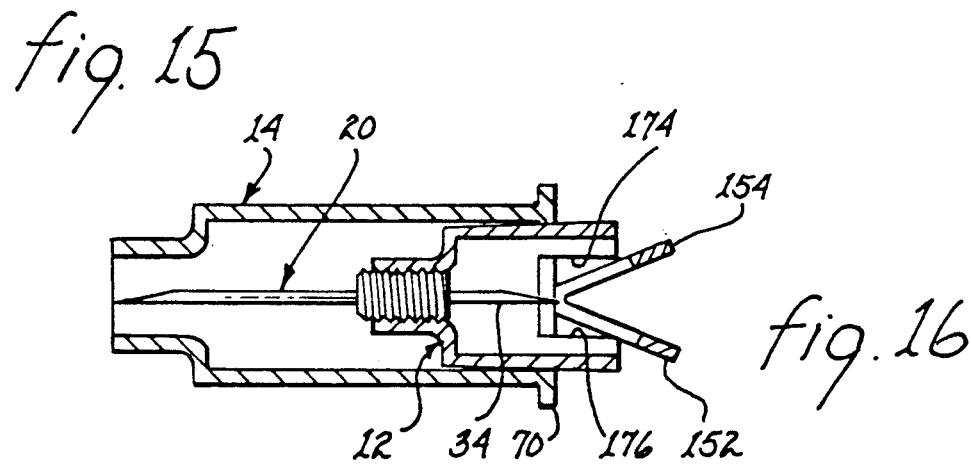
fig. 15
fig. 16
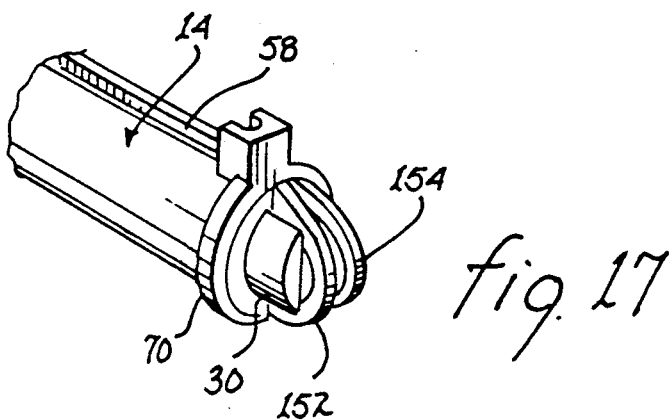
fig. 17

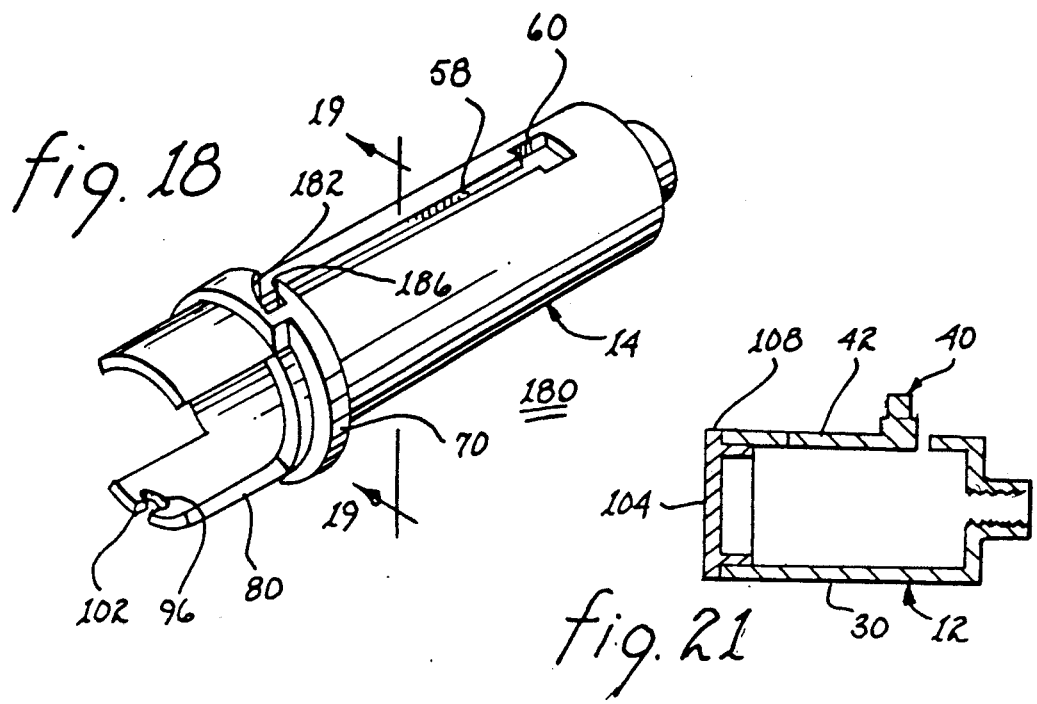
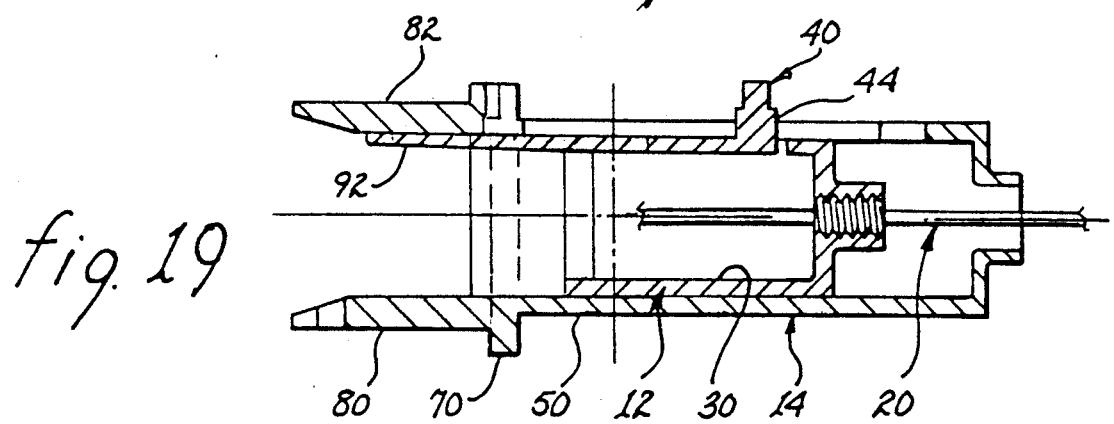
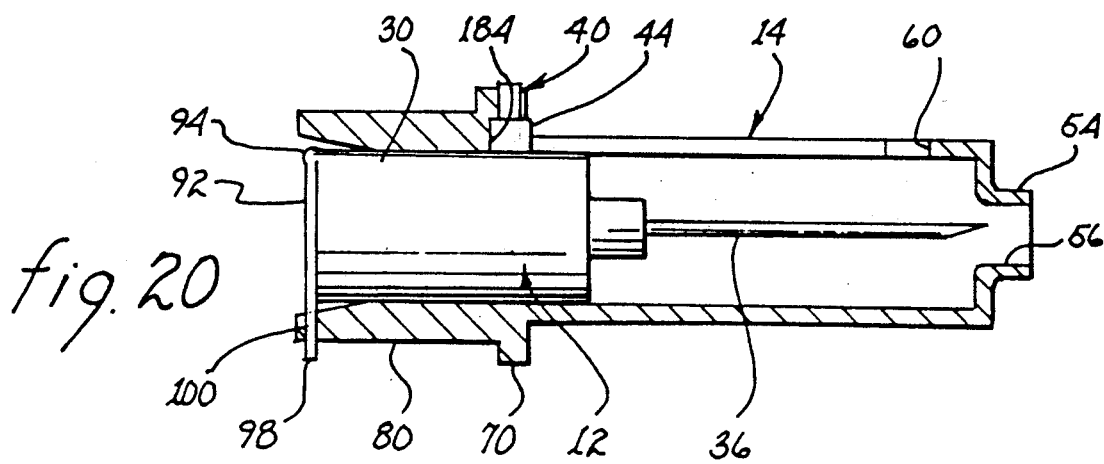

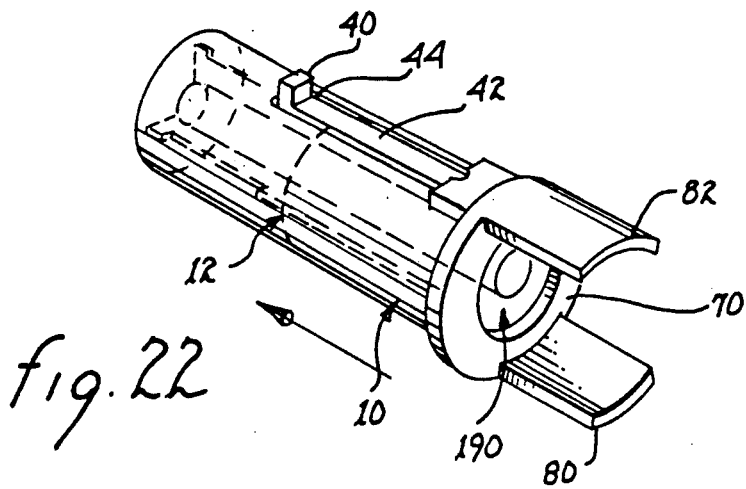
fig. 22
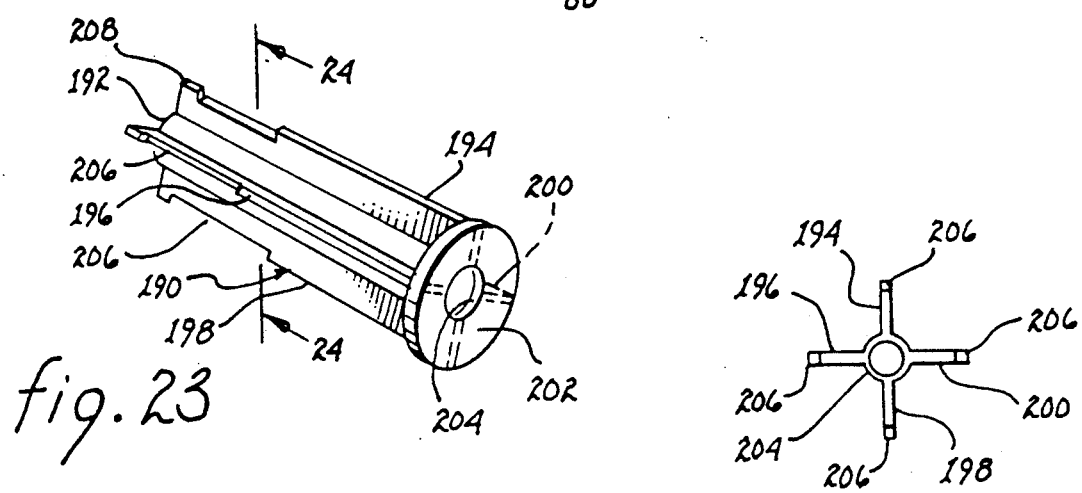
fig. 23
fig. 24
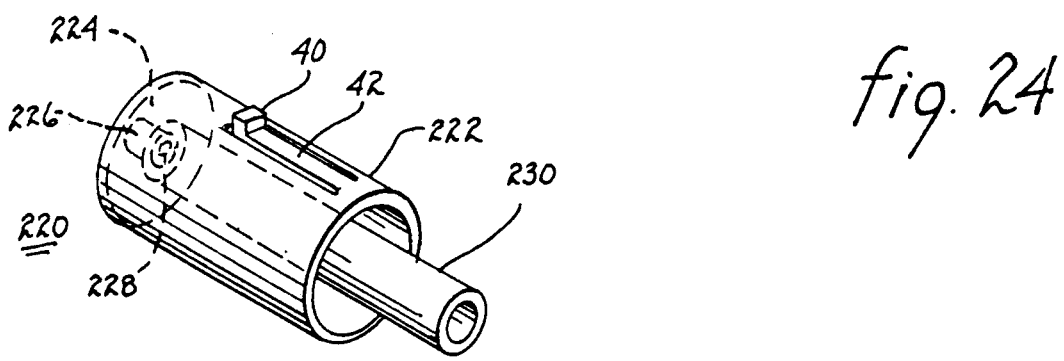
fig. 26
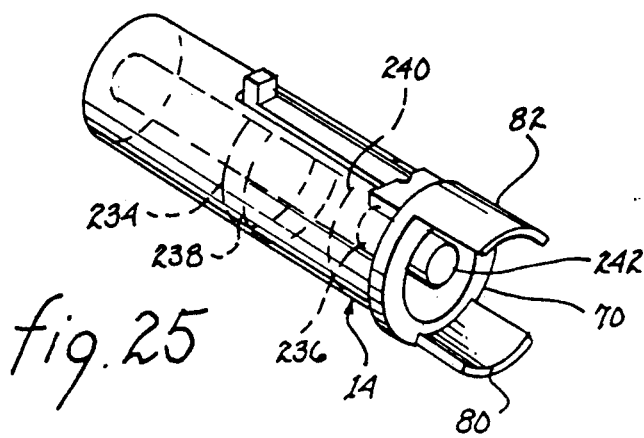
fig. 25

HOLDER FOR DOUBLE ENDED BLOOD COLLECTION RETRACTABLE NEEDLE

REFERENCE TO RELATED APPLICATIONS

The invention described herein is related to an invention described in copending patent applications entitled "INDWELLING PLACEMENT DEVICE WITH GUARD", Ser. No. 079,599, filed July 30, 1987, "NEEDLE GUARD FOR BODY SUBSTANCE ISOLATION", Ser. No. 160,150 filed Feb. 25, 1988, and in a PCT application entitled "NEEDLE GUARD", Ser. No. PCT/US87/01140 filed May 14, 1987, which applications are exclusively licensed to the present assignee.

BACKGROUND OF THE INVENTION

1. Field of the Invention

The present invention relates to a guard for blood collection needles and, more particularly, to a holder for a double ended needle axially translatable within a guard to protectively enclose the needle after use.

2. Description of the Prior Art

A needle shield which must be removed anteriorly from the hub of a double ended needle before the needle can be used for a blood collection procedure is well known. Remounting such a shield requires a user to insert the point of the needle into the open end of the shield and draw the shield posteriorly over the needle until the needle is fully enclosed and the shield lodged in place. Such a removable needle shield contains several limitations, including: (1) after blood has been drawn, medical personnel may occasionally delay capping of the needle with the shield, which delay creates a possibility of accidental contact with blood upon the needle, dripping blood or accidental puncture; (2) in order to recover the used needle, it is necessary to replace the shield over the pointed end of the needle, which replacement increases the risk to medical personnel of accidentally puncturing themselves; and (3) if a needle has been accidentally bent during a blood collection procedure or if the shield is replaced over the needle at an incorrect angle, the needle point may inadvertently pierce the side of the shield and puncture the fingers or hand.

In order to avoid problems attendant needle shields which must be remounted posteriorly from a location anterior of the needle point, various devices have been developed. A sleeve can be translatably mounted upon the barrel of a hypodermic syringe along with a locking arrangement to lock the sleeve in place upon anterior translation to enclose the needle within the sleeve. In another device, a single ended needle can be enclosed by drawing the barrel of an attached syringe posteriorly to draw the needle into a shield; for double ended needles, the collection tube, penetrably engaged with the posterior needle, is drawn posteriorly to locate the anterior needle within the shield. Various other known other devices also exist but each of them suffers from various impediments, including functional efficiency, manipulative ease under medical emergencies, structural integrity or cost.

SUMMARY OF THE INVENTION

A holder for penetrably engaging and retaining the hub of a commercially available double ended needle includes a cylindrical skirt extending posteriorly from a threaded boss in engagement with the hub. A cylinder having an aperture at one end for receiving and supporting the boss of the holder includes an axially aligned slot for penetrably receiving an upwardly extending resiliently mounted push button of the holder. The slot includes a first lock position for maintaining the holder and supported needle anteriorly positioned for use and a posterior lock for receiving and retaining the push button upon posterior translation of the holder to lock the anterior needle within the cylinder. Guards extend posteriorly from the cylinder to prevent accidental contact with the posterior needle while accommodating insertion and removal of a different length blood collection tubes. Various barriers may be incorporated to preclude access to the posterior needle subsequent to a medical procedure. The manipulation required to translate the anterior needle into the cylinder permits a one handed operation whereby medical personnel may use their other hand for tasks associated with the termination of a blood collection procedure.

It is therefore a primary object of the present invention to provide apparatus for rendering inaccessible a double ended blood collection needle after use.

Another object of the present invention is to provide a double ended needle supporting insert translatable within a cylinder to enclose the needle after use.

Still another object of the present invention is to provide apparatus for permitting one handed withdrawal and shielding of a double ended needle after a blood collection procedure.

Yet another object of the present invention is to provide a cylinder for receiving and protecting an insert mounted double ended needle which cylinder accommodates use of different length blood collection tubes without jeopardizing medical personnel coming into contact with the posterior needle.

A further object of the present invention is to provide a cylinder for receiving and protecting an insert mounted double ended needle, which insert accommodates use of different diameter blood collection tubes without jeopardizing medical personnel coming into contact with the posterior needle.

A yet further object of the present invention is to provide an inexpensive and easy to use apparatus for supporting and shielding a double ended needle.

A still further object of the present invention is to provide an insert for a double ended needle supporting holder axially translatable internally within a cylinder to removably receive a pediatric blood collection tube for use in a blood collection procedure.

A still further object of the present invention is to provide a method for receiving and protecting an insert mounted double ended needle within a cylinder, which cylinder accommodates use of different length blood collection tubes without jeopardizing medical personnel coming into contact with the posterior needle.

A still further object of the present invention is to provide a method for receiving and protecting an insert mounted double ended needle within a cylinder, which insert accommodates use of different diameter blood collection tubes without jeopardizing medical personnel coming into contact with the posterior needle.

These and other objects of the present invention will become apparent to those skilled in the art as the description thereof proceeds.

BRIEF DESCRIPTION OF THE DRAWINGS

The present invention will be described with greater specificity and clarity with reference to the following figures, in which:

FIG. 9 is a cross sectional view of a modification of the variant shown in FIG. 5;

FIG. 10 is an end view taken along lines 10—10, as shown in FIG. 9;

FIG. 11 is a cross sectional view illustrating the final position of the variant shown in FIG. 5;

FIG. 12 is a cross sectional view illustrating another embodiment of the double ended needle usable with the present invention;

FIG. 13 is a partial view illustrating the double ended needle shown in FIG. 12;

FIG. 14 is a second variant of the present invention;

FIG. 15 is a cross sectional view taken along lines 15—15, as shown in FIG. 14;

FIG. 16 is a top view illustrating the operation of the second variant shown in FIG. 14;

FIG. 17 is perspective end view of the final position of a double ended needle used in conjunction with the second variant shown in FIG. 14;

FIG. 18 illustrates a third variant;

FIG. 19 is a cross sectional view taken along lines 19—19, as shown in FIG. 18;

FIG. 20 is a cross sectional view illustrating the final position of the double ended needle of the third variant;

FIG. 21 is a cross sectional view of a further embodiment of the holder used in conjunction with the third variant;

FIGS. 22, 23 and 24 illustrate an adapter usable with a holder of the present invention to receive a pediatric tube; and FIGS. 25 and 26 illustrate a variant of the adapter for receiving a pediatric tube.

DESCRIPTION OF THE PREFERRED EMBODIMENT

Figure 1:
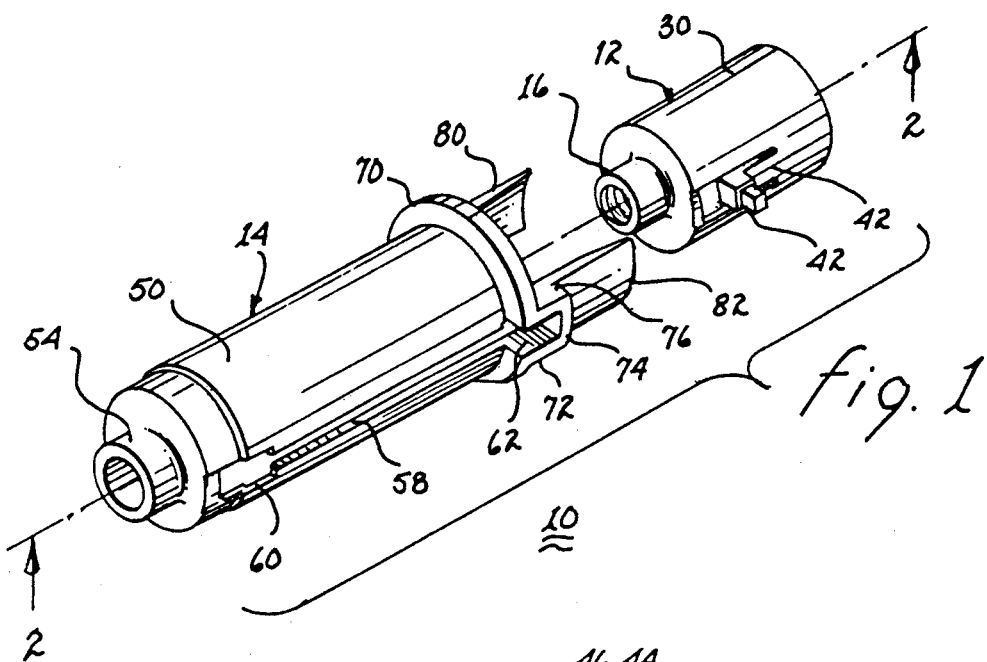
FIG. 1 is a perspective view of the two components of the present invention.
Figure 2:
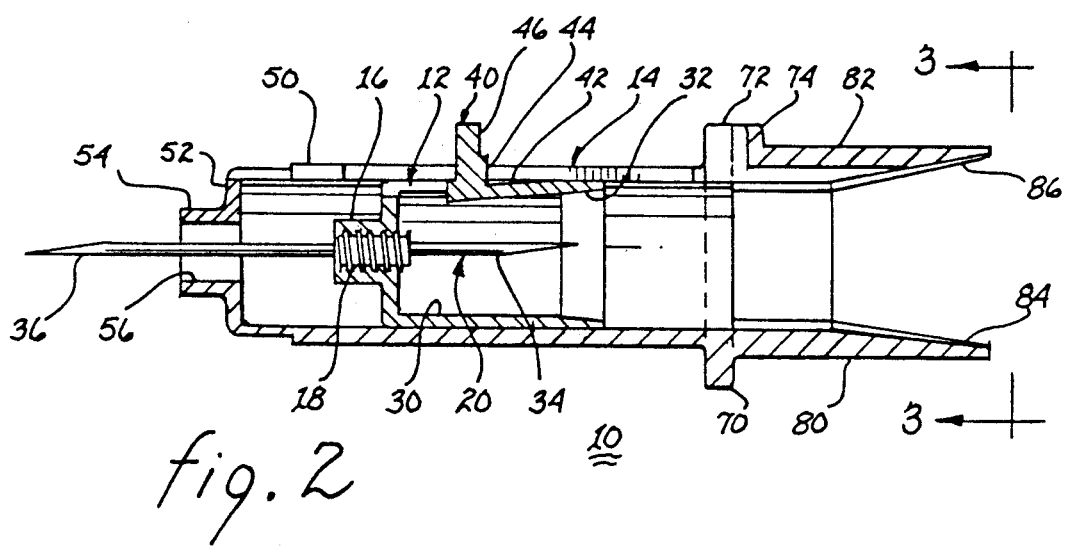
FIG. 2 is a cross sectional view taken along lines 2—2, as shown in FIG. 1.
Figure 4:
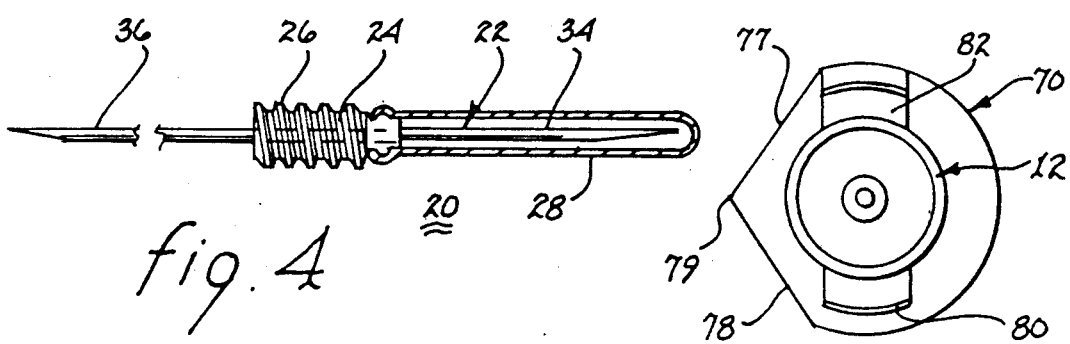
FIG. 4 is a side view of a commercially available double ended needle.

Referring to FIG. 1, there is shown a holder 10 for a double ended blood collection needle. This holder is used in conjunction with a blood collection tube to obtain blood specimens in the conventional manner. The holder includes an insert 12 for supporting a double ended needle and a cylinder 14 within which the insert is translatable to shield and lockably retain the double ended needle after use. Referring jointly to FIGS. 1, 2 and 4, further details of holder 10 will be described. Insert 12 includes a boss 16 having internal threads 18. A conventional commercially available double ended needle unit 20 includes a double ended needle 22 supported by a hub 24. A conventional valve 28 extends posteriorly from hub 24, as illustrated in FIG. 4, to enclose posterior needle 34 therein. The hub includes threads 26 for threadedly engaging threads 18 in boss 16. Upon such engagement, insert 12 will support double ended needle unit 20, as illustrated in FIG. 2. The insert includes a cylindrical skirt 30 having an interior diameter commensurate with that of a commercial blood collection tube. As particularly illustrated in FIG. 2, posterior needle 34 terminates short of the terminal end of skirt 30 and the skirt serves as a cover or shield extending about the posterior needle. Furthermore, terminal interior surface 32 of skirt 30 may be tapered radially outwardly to guide and provide for smooth insertion of a blood collection tube into insert 12 with commensurate penetration of posterior needle 34 with the stopper of the blood collection tube. A tab 40 extends radially outwardly from skirt 30 and is supported by a flexible resilient arm 42. The arm permits radially oriented displacement of the tab. Radial displacement of the tab will be resisted, but accommodated, by arm 42 which results in a bias being imposed upon the tab to maintain it in an initial position. As noted in FIG. 2 and in succeeding figures, arm 42 has an anterior free end supporting tab 40 and a posterior end affixed to skirt 30. This orientation permits minimal overlap between cylinder 14 and the insert when the insert is in the posterior position. Essentially the full length of the cylinder may be used to shield anterior needle 36 and the overall length of the cylinder will be minimized.

Cylinder 14 includes a sleeve 50 having a partially closed end 52 supporting a boss 54. The boss includes a passageway 56 sized commensurate with the external diameter of boss 16 to permit sliding engagement therebetween. A slot 58 extends axially along sleeve 50 between anterior expanded slot segment 60 and posterior expanded slot segment 62. Base 44 of tab 40 has a width commensurate with the width of each of segments 60 and 62. Upper end 46 of the tab has a width commensurate with that of slot 58. When insert 12 is disposed within cylinder 14 positioned to result in penetration of tab 40 with segment 60, base 44 of the tab will be proximate the peripheral edge of segment 60. Arm 42, supporting tab 40, will be essentially unbent. In order to translate tab 40 within slot 58, the tab must be depressed until upper end 46 engages the opposed sides of the slot. To effect such engagement, arm 42 will be bent downwardly by pressing upon the tab. Such downward bending will result in a bias imposed upon tab 40 to urge the tab outwardly. Upon translation of tab 40 along slot 58 into segment 62, the expanded width of the segment will permit outward translation of tab 40 urged by arm 42 to locate base 44 of the tab in contact with the peripheral edge of the segment.

An annular flange 70 extends about cylinder 14 from opposed sides of segment 62. Further outwardly extending walls 72, 76 and 74 extend from the opposed sides and posterior edge of segment 62. The radial extension of walls 72, 74 and 76 is greater than the height of tab 40 extending above the cylindrical surface of sleeve 50. Accordingly, access to tab 40 when the latter is disposed within segment 62 is restricted. With such restricted access, it would be difficult, without extraordinary procedures, to depress tab 40 and to concurrently apply an anteriorly oriented force to bring about anterior translation of the tab within slot 58. That is, for all practical purposes, tab 40 will be lockingly engaged within segment 62.

As will be evident by inspection, translation of tab 40 will result in commensurate translation of insert 12 within cylinder 14. During use of holder 10, insert 12 is in its anterior most position with tab 40 lockingly engaged with segment 60. Such locking engagement will prevent posterior translation of the insert in response to any axially oriented forces imposed upon anterior needle 36. On completion of the blood collection procedure, a phlebotomist holding holder 10 in one hand can depress tab 40 with finger or thumb of that hand and thereafter translate it posteriorly into segment 62. Upon such translation, anterior needle 36 will be drawn into cylinder 14 and posterior needle 34 is shielded by skirt 30 of insert 12. In this position, the holder shields the anterior needle and the posterior needle against inadvertent needle stick or contact with medical personnel. Upon posterior translation of insert 12, protection must be provided by skirt 30 to ensure against inadvertent needle stick by contact with posterior needle 34. To accommodate insertion and removal of short blood collection tubes, a pair of sidewalls 80 and 82 may be provided to extend posteriorly from diametrically opposed segments of cylinder 14. These segments may include inner surfaces 84, 86, respectively, tapering radially outwardly to guide and assist in insertion of a blood collection tube therebetween and into cylinder 14. Because the two sidewalls do not encircle an inserted blood collection tube, the blood collection tube, posteriorly of flange 70, is exposed on diametrically opposed sides intermediate the sidewalls and the blood collection tube can be readily grasped for withdrawal. The two sidewalls also serve two other important functions. First, they provide support to insert 12 when the latter is in the posterior position to prevent lateral wobble. Such wobble, if permitted, might cause tab 40 to become disengaged from segment 62. Second, the sidewalls tend to prevent an anteriorly oriented force from acting upon the insert. Such force, if great enough, might cause anterior translation of the insert from its locked posterior position with commensurate exterior of anterior needle 36 from within cylinder 14.

Figure 3:
FIG. 3 is an end view taken along lines 3—3, as shown in FIG. 2.
Figure 5:
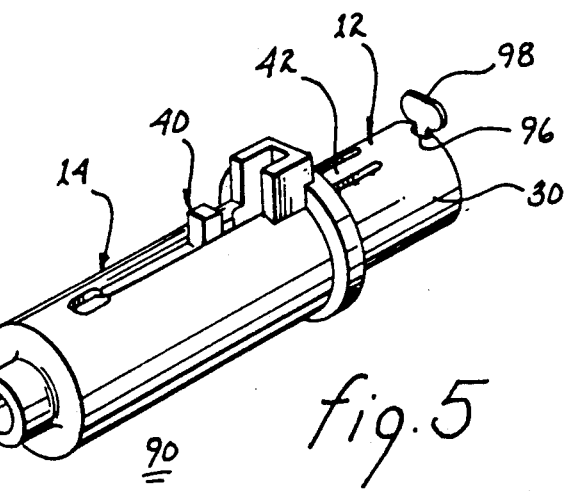
FIG. 5 illustrates a first variant of the present invention.
Figure 6:
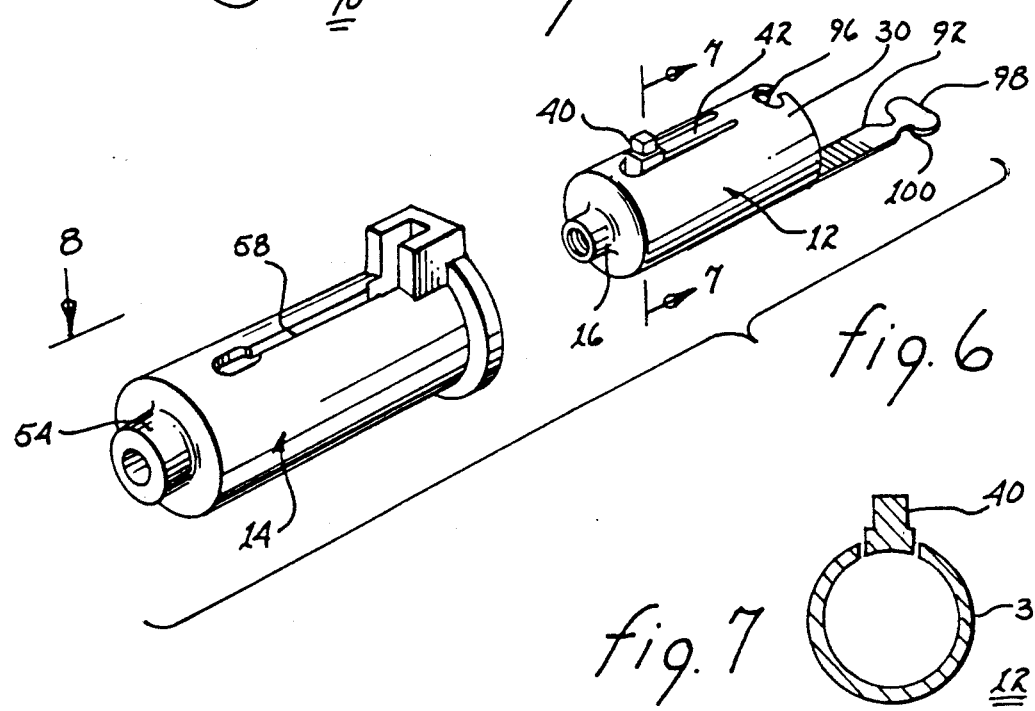
FIG. 6 illustrates the components of the variant shown in FIG. 5.
Figure 7:
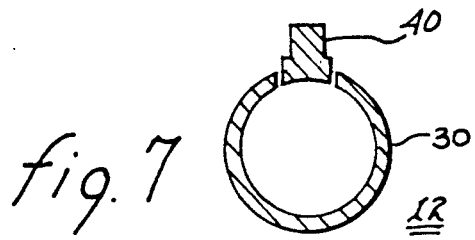
FIG. 7 is a cross sectional view taken along lines 7—7, as shown in FIG. 6.
Figure 8:
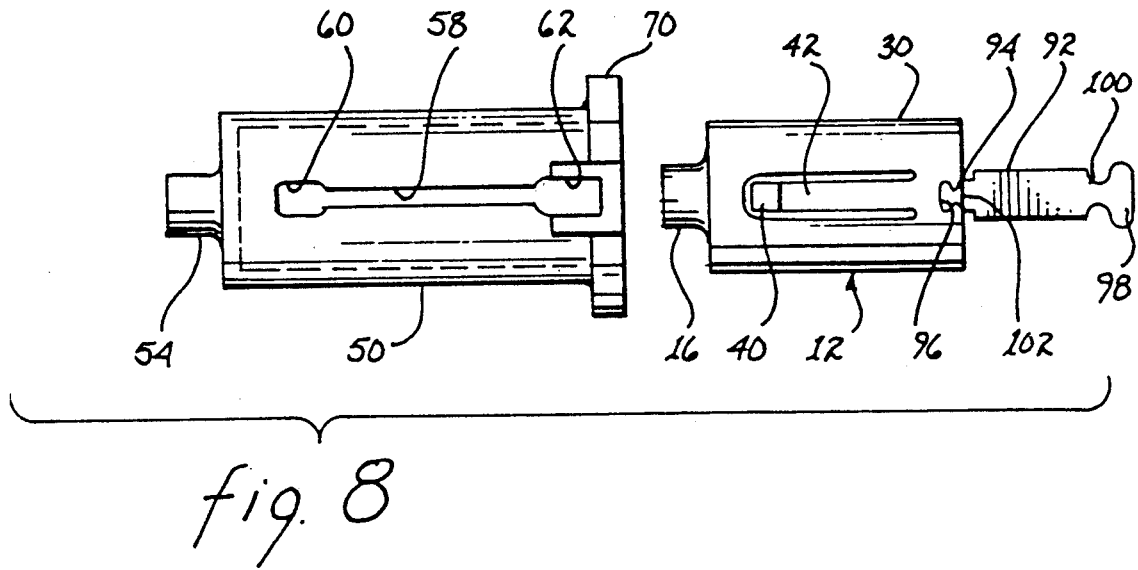
FIG. 8 is a top view taken along lines 8—8, as shown in FIG. 6.

To prevent holder 10 from rolling on a surface upon which it may be placed, flange 70 may be only partially circular, as illustrated in FIG. 3. The remaining segment of the flange may include one or more straight edges, such as edges 77, 78 intersecting at point 79. One or more of these straight edges will be an impediment to any rolling motion of the holder.

Referring jointly to FIGS. 5 to 8, there is shown a variant 90 of holder 10. With regard to elements common to both holder 10 and variant 90, the same reference numerals will be used. Cylinder 14 is devoid of sidewalls 80, 82 of holder 10. To shield the posterior needle upon posterior translation of insert 12 a strap 92 is employed to extend diametrically across the posterior edge of skirt 30. The strap is flexibly secured to or forms a part of skirt 30 at junction 94. At an approximately diametrically opposed location from the junction, a keyway 96 is formed in skirt 30. A key 98 disposed at the extremity of strap 92 includes a neck segment 100 sized commensurate with opening 102 of keyway 96. The length of strap 92 is maintained to draw key 98 into the keyway to an extent sufficient to displace neck 100 from opening 102 and thereby prevent the wider part of the key from passing through the opening. The width of strap 92 is maintained mostly sufficient to cover the posterior opening of skirt 30 and prevent inadvertent intrusion of a phlebotomist's finger or other body part.

Referring jointly to FIGS. 9, 10 and 11, a further variant 110 of holder 10 is illustrated. With regard to elements in variant 110 common with those of holder 10, identical reference numerals will be used. In the anterior position of insert 12 within cylinder 14, the insert is supported by the interior surface of sleeve 50. Additionally, boss 16 of the insert is lodged within passageway 56 of boss 54. The axial position of the insert is maintained by tab 40 being lockingly engaged within segment 60. Thus, insert 12 and the supported double ended needle 20 is relatively rigidly maintained in place. To further stabilize the insert in the anterior position, the respective diameters of the insert and the interior of the cylinder may be sized to produce an interfering fit. Upon posterior translation of the insert, certain positional fixation is provided by base 44 of tab 40 engaging segment 62 of slot 58. Further support is provided by the interior cylindrical surface of sleeve 50 engaging the exterior cylindrical surface of insert 12 remaining within cylinder 14. To further stabilize the insert in its posterior most position, a plurality of longitudinally oriented tapered posteriorly expanded ribs 112, 114, 116 and 118 may be formed in the interior surface of sleeve 50. These ribs will engage the exterior surface of insert 12 and tend to clamp the insert therebetween. Accordingly, when insert 12 is in its posterior most position, the longitudinal ribs will assist in stabilizing and rigidly retaining the insert in place. As particularly noted in FIG. 9, strap 92 extends posteriorly from skirt 30. Furthermore, it may be fully enclosed within cylinder 14 when insert 12 is in its anterior most position, as shown in FIG. 9. Upon posterior translation of insert 12, strap 92 may be rotated about junction 94 to engage key 98 with keyway 96.

Referring to FIGS. 12 and 13, there will be described guards 120, 122 for shielding anterior needle 36 and posterior needle 34 of double ended needle unit 20. As illustrated, the double ended needle is supported within a holder for a double ended needle, such as holder 10 particularly illustrated in FIGS. 1 and 2. However, it is to be understood that the guards could also be incorporated in variants of holder 10. Hub 24 is threadedly engaged with boss 16 of insert 12, as described previously. The relative length of boss 16 and hub 24 is selected to provide extension of the threaded hub anteriorly and posteriorly of boss 16. Guard 120 is hollow and includes a cavity 124 to receive and shield anterior needle 36. End 124 of the guard is closed and may include opposed flats 128 to assist in manual gripping of the guard. The posterior end of guard 120 includes interior threads 130 for threadedly engaging hub 24 anterior of boss 16. In this manner, guard 120 may be unscrewed from the hub to expose the anterior needle or screwed thereon to enclose the anterior needle therewithin. Guard 122 is hollow and includes a cavity 132 for receiving posterior needle 34 therein. End 134 is closed and may include opposed flats 136 for manual gripping purposes. The anterior end of the guard includes threads 138 for threadedly engaging the posterior exposed end of hub 24. Thereby, guard 122 may be unthreaded from the hub to expose the posterior needle or threaded thereon to shield the posterior needle. It is to be understood that guards 120, 122 could be readily adapted for use with the hubs of existing and commercially available double ended needles.

With various prior art devices having guards for enclosing a needle from the point of the needle, inadvertent needle stick may often occur. When using guards 120, 122 with holder 10, such needle stick is precluded for the following reasons. The guards would not be mounted upon hub 24 until insert 12 were in its posterior locked position. In this position, anterior needle 36 is enclosed within cylinder 14. By inserting guard 120 through aperture 56 in boss 54, the guard is guided onto the needle and the needle is sufficiently recessed to prevent contact with a user. The guide function performed by boss 54, in combination with the needle itself after penetration of the guard has occurred, will result in easy threaded engagement with hub 24. With regard to posterior needle 34, it will be enclosed within skirt 30 of insert 12 when the insert is in its posteriormost position. Any inadvertent contact with the posterior needle upon installation of guard 122 will not occur. Once posterior needle 34 has been partially inserted within guard 122, the guard will tend to be guided onto hub 24 where threaded engagement is readily effected.

Referring specifically to FIG. 13, there is illustrated a variant of guards 120, 122 wherein such guards may be used to maintain double ended needle 20 sterile prior to mounting in insert 12. Hub 24 is depicted as including an anteriorly extending threaded segment 140 for threaded engagement with guard 120. A similar posteriorly extending threaded segment 142 threadedly engages guard 122. The two guards may be sonic welded, as depicted by welds 144, 146, to hub 24. By twisting the guards relative to the hub, the respective welds may be broken to permit threaded disengagement of the guards.

The bevel of the anterior needle should be oriented upwardly during venipuncture. Holder 10 is most easily and readily used by a phlebotomist if tab 40 is oriented upwardly. Both of these desired conditions will always be present if insert 12 is manufactured to incorporate a double ended needle germanently secured to boss 16 in the preferred orientation.

By incorporating a double ended needle 22 with an insert 12 at the time of manufacture of the insert, several advantages attendant manufacture, distribution and use of holder 10 may be achieved. The costs associated with the manufacture of boss 16 having threads 18 may be avoided along with the costs attendant securing a threaded hub 26 with the double ended needle. The labor costs of manufacturing personnel or machines or of medical personnel joining the double ended needle with the insert are vitiated. The complete holder can be shipped and stored ready for use in individual packets or containers in a sterile state. In the packaged configuration, the insert would be lodged within cylinder 14 to locate tab 40 anteriorly of the second position (segment 62) at a position sufficiently posterior to retain anterior needle 36 disposed within the cylinder to protect medical personnel from accidental needle stick. When the holder was to be used, it would be removed from its sterile container. Prior to venipuncture, tab 40 would be translated to the first position (segment 60) to exteriorize the anterior needle and lock the double ended needle in place. Upon completion of the blood collection procedure, the anterior needle would be drawn into cylinder 14 by translating the tab to the second position, as discussed above.

Referring to FIGS. 14, 15, 16 and 17, a variant 150 of holder 10 will be described. The primary difference between variant 150 and holder 10 is the elimination of sidewalls 80, 82 in favor of wings 152, 154. Wing 152 is a semi circular arc 156 having ends 158, 160 flexibly or bendably secured to rear surface 162 of annular flange 70. Wing 154 includes a similar arc 164 having ends 166, 168 also secured to rear surface 162 of annular flange 70. Skirt 30 of insert 12 includes diametrically opposed insets 170, 172. Upon posterior translation of insert 12, as particularly illustrated in the cross sectional views shown in FIGS. 15 and 16, opposed sides 174, 176 of insets 170, 172 will bear against the anterior surfaces of arcs 156, 164 of wings 152, 154, respectively. Upon such engagement, with further posterior movement of insert 12, the wings will pivot posteriorly to a near parallel position with one another, as depicted in FIG. 16. The final angle between the wings is a function of the width of insets 170, 172 and the thickness of the two wings. In the posterior locked position of insert 12, wings 152, 154 will effectively preclude inadvertent contact by medical personnel with posterior needle 34 shielded by and within skirt 30 of insert 12.

Referring jointly to FIGS. 18 to 21, there is illustrated a further variant 180 of holder 10. With regard to common elements between holder 10 and variant 180, identical reference numerals will be employed. Cylinder 14 includes slot 58 having anterior segment 60 for lockingly engaging and retaining tab 40 lodged therein. Upon depression of the tab with commensurate downward bending of arm 42, the tab may be slid within slot 58 posteriorly with commensurate posterior movement of insert 12 within the cylinder. In proximity to annular flange 70, tab 40 will engage a channel 182 extending posteriorly and radially about the longitudinal axis of cylinder 14. By translating tab 40 into and along channel 182, it will be locked within the channel to prevent inadvertent anterior displacement of insert 12. At the terminal end of channel 182, an enlarged segment 184 (see FIG. 20) may be disposed to accommodate upward translation of tab 40 in response to the urging or bias provided by resilient arm 42. In this position, the tab is prevented from anterior movement by interference with channel wall 186 and it is prevented from radial or rotational movement about the longitudinal axis of cylinder 14 by segment 184 interferingly engaging base 44 of the tab.

To more effectively guard against inadvertent insertion of a body part by medical personnel through the posterior end of skirt 30 of insert 12, a strap 92 may be deployed to extend thereacross. The strap is pivotally attached to skirt 30 at junction 94. It includes a key 98 having a neck 100, like that depicted in FIGS. 6 and 8. A keyway 96 is disposed in sidewall 80. The keyway includes an opening 102 for receiving neck 100. Upon locking engagement of strap 92 with sidewall 80, not only does a barrier extend across the posterior opening of skirt 30 but insert 12 is further lockingly engaged with cylinder 14 in the posteriormost position of the insert. Such further locking of the insert will add insurance against inadvertent anterior relocation of the insert which might result in exposure of anterior needle through passageway 56 in boss 54. FIG. 21 illustrates a cap 104 for guarding the insert against intrusion The cap has an annular ridge 106 for engaging the interior of skirt 30. A radial flange 108 extends from the ridge adjacent the terminal end of the skirt to locate the cap in place. A variant of the cap having an annular ridge for engaging the skirt circumferentially is also contemplated.

As mentioned above, standard blood collection tubes of a constant diameter come in two lengths. In addition, certain blood collection tubes, referred to as pediatric tubes, are approximately 10 mm in diameter. To make a blood collection tube holder 10 of a size to receive pediatric tubes would render such holder too small to be readily and easily usable by a phlebotomist or other medical personnel. Referring jointly to FIGS. 22, 23 and 24 there is illustrated an adapter 190 for use with any one of the above described blood collection tube inserts or variants thereof. Since holder 10 (see FIGS. 1 and 2) is typical, it is illustrated in FIG. 22 with adapter 190 disposed within insert 12 of the holder. The adapter includes a tube 192 sized to receive a pediatric tube (not shown). A plurality of flanges or wings 194, 196, 198 and 200 extend radially therefrom; these wings may be equiangularly positioned, as illustrated. To add robustness to the wings and to join them with one another, an apertured disk 202 is attached to the proximal end of tube 192 and each of wings 194, 196, 198 and 200. Aperture 204 in the disk is at least large enough in diameter to accept a pediatric tube. Preferably, the aperture is commensurate with the diameter of tube 192 to permit attachment of the disk with the proximal end of the tube.

Adapter 190 is installed within insert 12 in frictional engagement therewith in order that it be retained in place during normal use of holder 10. To ensure that wings 194, 196, 198 or 200 do not interfere with radial inward travel of tab 40 or arm 42 associated therewith, detents 206 may be developed in each of the wings proximate the location of base 44 of tab 40. Moreover, a section of the edge of each of wing posterior of the detent must be of reduced size in order to accommodate radial inward movement of arm 42 associated with tab 40 if the arm does not extend commensurate with the detent. The anterior end 208 of each of the wings may be radially extended commensurate with the interior diameter of cylinder 14 to obtain a reasonably tight friction fit therewith. Similarly, the diameter of disk 202 is selected commensurate with the corresponding interior diameter of skirt 30 to obtain a friction fit therewith. With such friction fit, adapter 190 will not become dislodged from within insert 12 during normal use.

By incorporating adapter 190, holder 10, or one of its variants, can be used for either normal diameter sized blood collection tubes by omitting the adapter or with pediatric tubes by inserting the adapter. Furthermore, the insertion and removal of the adapter may be quickly made.

Referring jointly to FIGS. 25 and 26 there is illustrated a variant insert 220 of adapter 190. Herein, variant insert 220, much like insert 12, includes radially displacable tab 40 supported upon resilient arm 42 for engagement with cylinder 14 in the manner described above. Variant insert 220 includes a closed end defined by a wall 224 extending across the anterior end of the variant insert. The wall supports a hollow boss 226 having internal threads 228 for engaging the threaded hub of a double ended needle unit 20. A tube 230 has an inside diameter commensurate with that of a pediatric tube to permit insertion therein and removal therefrom of a pediatric tube. As illustrated, tube 230 extends posteriorly from wall 224.

As particularly illustrated in FIG. 25, there is shown a cylinder 14 similar to that of holder 10 shown in FIGS. 1 and 2. Variant insert 220 has been inserted within cylinder 14. The variant insert is shown in two positions. In the anteriormost position, the posterior end of the skirt of variant insert 220 is depicted by dashed line 234 and the terminal end of tube 230 is depicted by dashed line 236. In the posteriormost position of variant insert 220, the anterior and posterior ends of the skirt of the variant insert are depicted by dashed lines 238, 240, respectively. The posterior location of the terminal end of tube 230 is identified with numeral 242. It may be noted that sidewalls 80 and 82 are illustrated as extending rearwardly from the outer diameter of flange 70. It is contemplated that a more radially inward location, such as depicted in FIG. 2, is preferable.

With the use of variant insert 220, holder 10 is usable primarily only with pediatric tubes; however, the variant insert may be replaced by insert 12. Depending upon the nature of the practice of particular phlebotomists or medical personnel, variant insert 220 may be more practical than the use of an adapter 190 in a holder, such as holder 10 or one of the above described variants of the holder.

While the principles of the invention have now been made clear in an illustrative embodiment, there will be immediately obvious to those skilled in the art many modifications of structure, arrangement, proportions, elements, materials and component used in the practice of the invention which are particularly adapted for specific environments and operating requirement without departing from those principles.

We claim:

1. A blood collection tube holder used in a blood collection procedure for supporting and shielding a double ended needle, which double ended needle includes an anterior needle and a posterior needle, said holder comprising in combination:
   a) a cylinder for enclosing the anterior needle of the double ended needle on termination of the blood collection procedure, said cylinder having an anterior end and a posterior end;
   b) an insert for shielding the posterior needle of the double ended needle during and on termination of the blood collection procedure and for removably retaining a blood collection tube, said insert being axially translatable within said cylinder from a first position proximate the anterior end of said cylinder to a second position proximate the posterior end of said cylinder on termination of the medical procedure, said insert having an anterior end and a posterior end;
   c) means disposed in the anterior end of said insert for maintaining the double ended needle;
   d) first means for locking said insert in the first position while said holder is used during the blood collection procedure to prevent posterior translation of said insert and the double ended needle during removal of the blood collection tube; and
   e) second means for locking said insert in the second position, said second locking means including: a flexible resilient arm extending from a posterior fixed end in said insert to an anterior free end, a tab extending radially outwardly from the free end of said arm and a longitudinally aligned slot having a posterior end and an anterior end, said slot being disposed in said cylinder for receiving said tab, means for preventing translation of said tab along said slot from the posterior end and toward the anterior end of said slot in response to outward radial displacement of the free end of said arm, said arm being responsive to an anteriorly oriented force applied to insert to urge outward radial translation of the free end of said arm to more forcefully urge locking means to lock said insert in the second position.

2. The blood collection tube holder as set forth in claim 1 wherein said tab includes an expanded cross section base of a width greater than said slot and wherein said slot includes an expanded segment disposed anteriorly and defining the first position for receiving said base in response to radial outward movement urged by said arm and for precluding translation posteriorly of said tab relative to said slot and said insert relative to said cylinder.

3. The blood collection tube holder as set forth in claim 2 wherein said slot includes a further expanded segment disposed posteriorly and defining the second position for receiving said base in response to radial outward movement urged by said arm and for precluding translation anteriorly of said tab relative to said slot and said insert relative to said cylinder.

4. The blood collection tube holder as set forth in claim 1 wherein said cylinder includes at least one posteriorly extending sidewall for accommodating insertion and access to a blood collection tube within said cylinder while guarding the posterior needle of the double ended needle against contact by medical personnel.

5. The blood collection tube holder asset forth in claim 4 including a pair of diametrically opposed ones of said side walls.

6. The blood collection tube holder as set forth in claim 1 including means for restraining rolling of said cylinder upon a surface.

7. The blood collection tube holder as set forth in claim 1 including an anterior guard for receiving and releasably retaining the anterior needle of the double ended needle.

8. The blood collection tube holder as set forth in claim 1 including a posterior guard for receiving and releasably retaining the posterior needle of the double ended needle.

9. The blood collection tube holder as set forth in claim 8 including an anterior guard for receiving and releasably retaining the anterior needle of the double ended needle.

10. The blood collection tube holder as set forth in claim 9 including means for threadedly engaging said anterior guard and said posterior guard with the hub of the double ended needle.

11. The blood collection tube holder as set forth in claim 1 including means for frictionally engaging said insert with said cylinder when said insert is in the first position.

12. The blood collection tube holder as set forth in claim 1 including means for frictionally engaging said insert with said cylinder when said insert is in the second position.

13. The blood collection tube holder as set forth in claim 1 wherein said insert includes an internally threaded hollow boss for threadedly engaging the hub o: the double ended needle.

14. The blood collection tube holder as set forth in claim 13 wherein said cylinder includes a hollow boss for receiving and supporting said boss of said insert when said insert is in the first position.

15. The blood collection tube holder as set forth in claim 1 including a adapter for insertion within said insert to receive and support a pediatric tube.

16. The blood collection tube holder as set forth in claim 15 wherein said adapter includes means disposed anteriorly and posteriorly for positioning said adapter within said insert.

17. The blood collection tube holder as set forth in claim 15 wherein said adapter includes a sleeve for receiving the pediatric tube and means for supporting said tube within said insert.

18. The blood collection tube holder as set forth in claim 1 wherein said insert includes means for supporting a pediatric tube.

19. The blood collection tube holder as set forth in claim 18 wherein said supporting means includes an endwall and a tube extending from said endwall for receiving the pediatric tube.

20. The blood collection tube holder as set forth in claim 1 wherein the blood collection tube is partially supported by said cylinder when said insert is in the first position.

21. The blood collection tube holder as set forth in claim 1 wherein the double ended needle includes a posterior needle extending into said insert and wherein said insert includes a skirt extending posteriorly of the terminal end of the posterior needle.

22. The blood collection tube holder as set forth in claim 21 including strap means extendable across the posterior end of said skirt after removal of the blood collection tube for protecting medical personnel against inadvertent contact with the terminal end of the posterior needle.

23. The blood collection tube holder as set forth in claim 22 wherein said protecting means interconnects said insert with said cylinder.

24. The blood collection tube holder as set forth in claim 22 wherein said protecting means is formed integral with said insert.

25. The blood collection tube holder as set forth in claim 1 wherein said cylinder includes means extending posteriorly of said cylinder for guarding said insert against an imposed force tending to cause anterior translation of said insert from the second position.

26. The blood collection tube holder as set forth in claim 25 wherein said guarding means includes means for inhibiting lateral wobble of said insert with respect to the longitudinal axis of said cylinder.

27. The blood collection tube holder as set forth in claim 1 wherein the double ended needle is formed integral with said insert.

28. The blood collection tube holder as set forth in claim 1 including a boss disposed at the anterior end of said insert for supporting the double ended needle.

29. The blood collection tube holder as set forth in claim 1 wherein the double ended needle is formed integral with said boss.

30. The blood collection tube holder as set forth in claim 1 wherein said insert extends posteriorly of said cylinder when said insert is in the second position and wherein said insert is only partially supported by said cylinder.

31. Apparatus for use during a medical procedure to draw blood, said apparatus comprising in combination:
a) an insert for supporting a double ended needle having an anterior needle and a posterior needle, said insert including a circular sidewall for shielding the posterior needle and for receiving a blood collection tube in penetrable engagement with the posterior needle;
b) a cylinder for receiving said insert and for accommodating translation of said insert from a first position wherein the anterior needle of the double ended needle extends from within said cylinder ready to be used in the medical procedure to a second position wherein the anterior needle is disposed within said cylinder and shielded against inadvertent contact by medical personnel;

c) means for retaining said insert in the first position during the medical procedure, said retaining means including an arm formed as part of said side wall and having a posterior end fixed to said sidewall and a free end disposed anteriorly of the fixed end, a tab extending radially outwardly from the free end, a slot having a posterior end and an anterior end, said slot extending longitudinally in said cylinder for receiving said tab and for accommodating translation of said tab during translation of said insert relative to said cylinder, means disposed in the vicinity of the free end of said arm for interfering with translation of said tab along said slot absent a radial inward displacement of the free end of said arm relative to said slot, a first laterally expanded segment disposed at the anterior end of said slot for receiving said interfering means in response to outward radial movement urged by said arm and for retaining said tab to lock said insert in the first position, and d) second means for retaining said insert in the second position on completion of the medical procedure, said second retaining means including a second laterally expanded segment disposed at the posterior end of said slot for receiving said interfering means in response to outward radial movement urged by said arm and for retaining said tab to lock said insert in the second position, said arm being responsive to an anteriorly oriented force imposed upon said insert to urge outward radial movement of said tab to more firmly engage said interfering means into locking engagement with said second laterally expanded segment.

32. The apparatus as set forth in claim 31 including means for restricting access to said tab when said tab is positioned in engaged relationship with said second expanded segment.

33. The apparatus as set forth in claim 32 wherein said restricting means comprises two sidewalls and an end wall.

34. The apparatus as set forth in claim 31 wherein said insert includes an integrally attached double ended needle and wherein said accommodating means includes means for positioning said insert intermediate the first and second positions prior to use and for positioning said insert therefrom to the first position in anticipation of use.

35. The apparatus as set forth in claim 31 wherein said slot includes a laterally expanded segment at each of the anterior and the posterior ends of said slot and wherein said tab includes a laterally expanded base for engaging said laterally expanded segments at the anterior and posterior ends of said slot.

36. A method for shielding the anterior and posterior needles of a double ended blood collection needle on completion of a blood collection procedure for collecting blood in a blood collection tube penetrably engaged with the posterior needle of the double ended needle, said method comprising the steps of:

a) translating an insert, which insert removably receives the blood collection tube, supports the double ended blood collection needle and maintains shielded the posterior needle, from an anterior position to a posterior position to draw the anterior needle into the cylinder;

b) unlocking the insert from the anterior position prior to exercise of said step of translating, said step of unlocking including the step of pushing a tab flexibly attached to the insert radially inwardly to disengage the tab from an anterior location of a slot disposed axially along the cylinder, which slot is of sufficient width to receive the tab, said step of pushing including the step of radially displacing the free anterior end of an arm from the sidewall of the insert and extending anteriorly from the insert, which free end supports the tab and biases the tab radially outwardly from the insert;

c) said step of translating comprising the step of displacing the tab along the slot after disengaging the tab from the anterior location of the slot;

d) positioning the tab at a posterior location of the slot to locate the insert in the posterior position; and e) urging the tab radially outwardly in response to an anteriorly oriented force applied to the insert to more firmly lock the tab at the posterior location of the slot and to lock the insert in the posterior position.

37. The method as set forth in claim 36 including the step of adapting the insert to receive and to support a selected one of a conventional blood collection tube and a pediatric blood collection tube.

38. The method as set forth in claim 36 wherein the double ended needle is integral with the insert and including the step of initially positioning the insert intermediate the anterior and the posterior positions and the step of repositioning the insert in the anterior position in anticipation of carrying out the blood collection procedure.

39. A blood collection tube holder adapted to support a double ended needle with a threaded hub for use in blood collection procedures, said holder comprising in combination:

a) a cylinder for enclosing the anterior needle of the double ended needle on termination of the medical procedure, said cylinder having an anterior end and a posterior end;

b) an insert for removably retaining a blood collection tube, said insert being axially translatable within said cylinder from a first position proximate the anterior end of said cylinder to a second position proximate the posterior end of said cylinder on termination of the medical procedure, said insert having an anterior end and a posterior end;

c) a boss disposed in said insert for maintaining the hub of the double ended needle;

d) means for locking said insert in the first position to use said holder during the blood collection procedure and for locking said insert in the second position to retain the anterior needle of the double ended needle within said cylinder on completion of the blood collection procedure; and e) said cylinder including at least one posteriorly extending wing for accommodating insertion and access to a blood collection tube within said cylinder while guarding the posterior needle of the double ended needle against contact by medical personnel when said insert is in the second position, said insert including a posteriorly extending skirt having an inset for receiving and posteriorly aligning said wing upon translation of said insert posteriorly.

40. The blood collection tube holder as set forth in claim 39 including a pair of said wings, said inset being configured to engage said pair of wings.

41. The blood collection tube holder as set forth in claim 40 wherein said cylinder includes an annular flange and wherein each of said wings includes opposed ends secured to said flange.

42. The blood collection tube holder as set forth in claim 41 including a pair of diametrically opposed insets in said skirt for engaging said pair of wings.

43. A blood collection tube holder for supporting and shielding a double ended needle used in blood collection procedures, which double ended needle includes an anterior needle and a posterior needle, said holder comprising in combination:
   a) a cylinder for enclosing the anterior needle on termination of the blood collection procedure, said cylinder having an anterior end and a posterior end;
   b) an insert for shielding the posterior needle during and on termination of the blood collection procedure and for removably retaining a blood collection tube, said insert being axially translatable within said cylinder from a first position proximate the anterior end of said cylinder to a second position proximate the posterior end of said cylinder;
   c) means for securing the double ended needle with said insert;
   d) means for locking said insert in the first position to maintain the anterior needle extended from within said cylinder and for locating said insert in the second position to maintain the anterior needle retracted within said cylinder; and
   e) said locking means including a slot having an anterior end and a posterior end, said slot being disposed within said cylinder, an arm having an end affixed to said insert and a free end disposed anteriorly of the fixed end, tab means extending from the free end of said arm and including an expanded base of a width greater than said slot and a tip in penetrable engagement with said slot, a first laterally expanded segment disposed at the anterior end of said slot for receiving the expanded base of said tab in response to a radial outward force exerted by said arm to lock said insert in the first position, a second laterally expanded segment disposed at the posterior end of said slot for receiving the expanded base of said tab in response to a radial outward force exerted by said arm to lock said insert in the second position, said arm being responsive to an anteriorly oriented force exerted upon said insert when said insert is in the second position to urge radial outward movement of said tab and more firmly lock said tab with said second expanded segment.

44. The apparatus as set forth in claim 43 wherein said arm is an integral part of said insert.

45. The apparatus as set forth in claim 43 wherein the length of said cylinder is insufficient to enclose the double ended needle.

46. The apparatus as set forth in claim 45 wherein said insert is extendable posteriorly of said cylinder in order to enclose the double ended needle within the combination of said cylinder and said insert.

* * * * *